United States Patent
Power et al.

(10) Patent No.: US 12,210,820 B2
(45) Date of Patent: *Jan. 28, 2025

(54) INTEGRATED DATA CAPTURE USING ALIASING SCHEMES

(71) Applicant: CERNER INNOVATION, INC., North Kansas City, MO (US)

(72) Inventors: Kevin M. Power, Kansas City, MO (US); Marsha Laird-Maddox, Kansas City, MO (US); Sara D. Boswell, Blue Springs, MO (US)

(73) Assignee: CERNER INNOVATION, INC., Kansas City, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/084,168

(22) Filed: Dec. 19, 2022

(65) Prior Publication Data

US 2023/0122360 A1   Apr. 20, 2023

Related U.S. Application Data

(60) Continuation of application No. 14/979,985, filed on Dec. 28, 2015, now Pat. No. 11,562,127, which is a division of application No. 13/939,406, filed on Jul. 11, 2013, now abandoned.

(51) Int. Cl.
| | |
|---|---|
| *G06F 40/174* | (2020.01) |
| *G16H 10/20* | (2018.01) |
| *G16H 10/60* | (2018.01) |
| *G16H 15/00* | (2018.01) |

(52) U.S. Cl.
CPC .......... *G06F 40/174* (2020.01); *G16H 10/20* (2018.01); *G16H 10/60* (2018.01); *G16H 15/00* (2018.01)

(58) Field of Classification Search
None
See application file for complete search history.

(56) References Cited

U.S. PATENT DOCUMENTS

| | | | |
|---|---|---|---|
| 6,256,643 B1 * | 7/2001 | Cork | A61M 1/3693 |
| 2002/0187496 A1 * | 12/2002 | Andersson | G16B 50/00 |
| | | | 435/6.14 |
| 2002/0194154 A1 * | 12/2002 | Levy | G16B 50/00 |

(Continued)

FOREIGN PATENT DOCUMENTS

CA   2334169 C   * 11/2005   ........... G06F 17/243

OTHER PUBLICATIONS

S. Trent Rosenbloom, MD, MPH, Jonathan Grande, BS, Antoine Geissbuhler, MD, Randolph A. Miller, MD, Experience in Implementing Inpatient Clinical Note Capture via a Provider Order Entry System, Journal of the American Medical Informatics Association, vol. 11, Issue 4, Jul. 2004, pp. 310-315. (Year: 2004).*

*Primary Examiner* — Lena Najarian
(74) *Attorney, Agent, or Firm* — Kraguljac Law Group, LLC

(57) ABSTRACT

Methods, systems, and computer-storage media are provided for using a generic aliasing scheme to facilitate electronic transcription of groups of clinical event data extracted from an electronic medical record to case report forms associated with clinical studies. The generic aliasing scheme is also used to electronically transcribe documentation of task completion to case report forms associated with the clinical studies.

20 Claims, 4 Drawing Sheets

(56) References Cited

U.S. PATENT DOCUMENTS

| | | | | |
|---|---|---|---|---|
| 2003/0046114 A1* | 3/2003 | Davies | ................... | G16Z 99/00 |
| | | | | 705/3 |
| 2003/0208490 A1* | 11/2003 | Larrea | ................... | G06F 16/252 |
| | | | | 707/999.009 |
| 2006/0293919 A1* | 12/2006 | Morlet | ................... | G16H 70/40 |
| | | | | 715/236 |
| 2007/0239484 A1* | 10/2007 | Arond | ................ | G06Q 10/0637 |
| | | | | 705/2 |

\* cited by examiner

INTEGRATED DATA CAPTURE USING ALIASING SCHEMES

CROSS-REFERENCE TO RELATED APPLICATIONS

This application is a continuation application of U.S. patent application Ser. No. 14/979,985, filed Dec. 28, 2015, entitled "Integrated Data Capture Using Aliasing Schemes"; which is a divisional of U.S. patent application Ser. No. 13/939,406, filed Jul. 11, 2013, entitled "Integrated Data Capture Using Aliasing Schemes." The aforementioned application is hereby incorporated by reference herein.

BACKGROUND

Clinical studies are scientific studies that test how a new medicine or a new treatment works in humans. Based on the outcomes of these studies, clinicians are able to find new and better ways to prevent, detect, diagnose, control, and treat diseases. Clinical studies often rely on clinical event data collected at healthcare facilities and stored in electronic medical record (EMR) systems associated with the healthcare facilities. Integrated data capture is used to electronically transcribe clinical event data culled from EMRs to case report forms associated with the clinical study. Previously, programs used by integrated data capture systems specified only a limited number of discrete data elements to pull from the EMR systems. If a clinical study required more than this limited number of data elements, a custom program would have to be created—a time-consuming and expensive endeavor. Moreover, previous programs were limited in that they were not designed to group clinical event data together or gather data regarding task documentation from the EMR. For example, previous programs would be unable to gather data regarding whether informed consent was documented for a particular clinical study.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief and at a high level, this disclosure describes, among other things, methods, systems, and computer-storage media for using aliasing schemes to facilitate electronic transcription of clinical event data extracted from an EMR to case report forms associated with one or more clinical studies. A generic aliasing scheme that is applicable to multiple, disparate clinical studies is defined. The generic aliasing scheme comprises at least a first field for specifying a clinical event type or group such as, for example, "vital signs," a second field for specifying a particular item of clinical event data within the clinical event group, and an optional third field that specifies one or more suffixes that describe how the clinical event data within the clinical event group is grouped after extraction from the EMR. The grouping may be based on the time and date when the data was collected, a relationship between a set of data elements and a parent event, or on whether a task was completed with respect to a data element. The groups are presented to a user on a user interface, and the user can select one or all of the groups to import to a case report form. Once a group(s) is selected, it is automatically imported to appropriate fields on the case report form based on the specified aliasing scheme.

BRIEF DESCRIPTION OF THE DRAWINGS

Embodiments are described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, systems, and computer-storage media for using aliasing schemes to facilitate electronic transcription of clinical event data extracted from an EMR to case report forms associated with one or more clinical studies. A generic aliasing scheme that is applicable to multiple, disparate clinical studies is defined. The generic aliasing scheme comprises at least a first field for specifying a clinical event type or group such as, for example, "vital signs," a second field for specifying a particular item of clinical event data within the clinical event group, and an optional third field that specifies one or more suffixes that describe how the clinical event data within the clinical event group is grouped after extraction from the EMR. The grouping may be based on the time and date when the data was collected, a relationship between a set of data elements and a parent event, or on whether a task was completed with respect to a data element. The groups are presented to a user on a user interface, and the user can select one or all of the groups to import to a case report form. Once a group(s) is selected, it is automatically imported to appropriate fields on the case report form based on the specified aliasing scheme.

Figure 1:
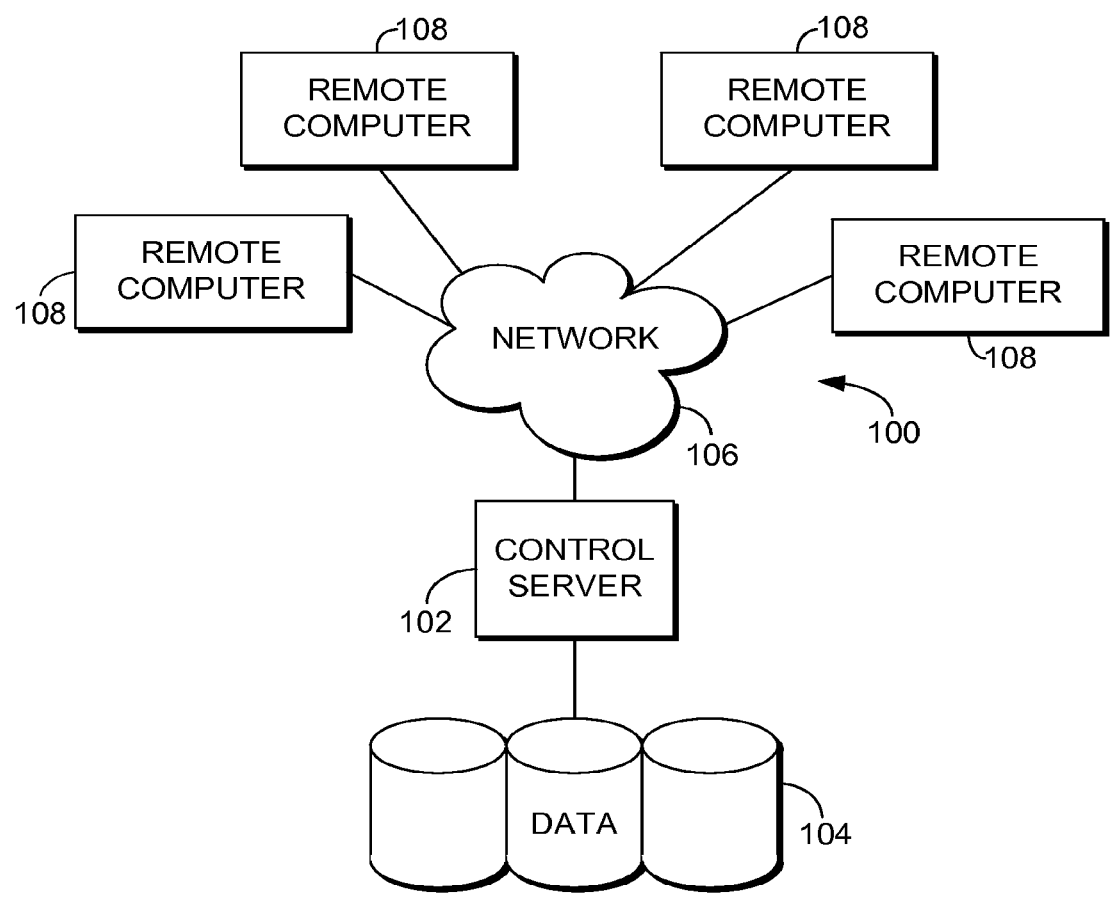
FIG. 1 is a block diagram of an exemplary computing environment suitable to implement embodiments of the present invention.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise non-transitory computer storage media and communication media. Non-transitory computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
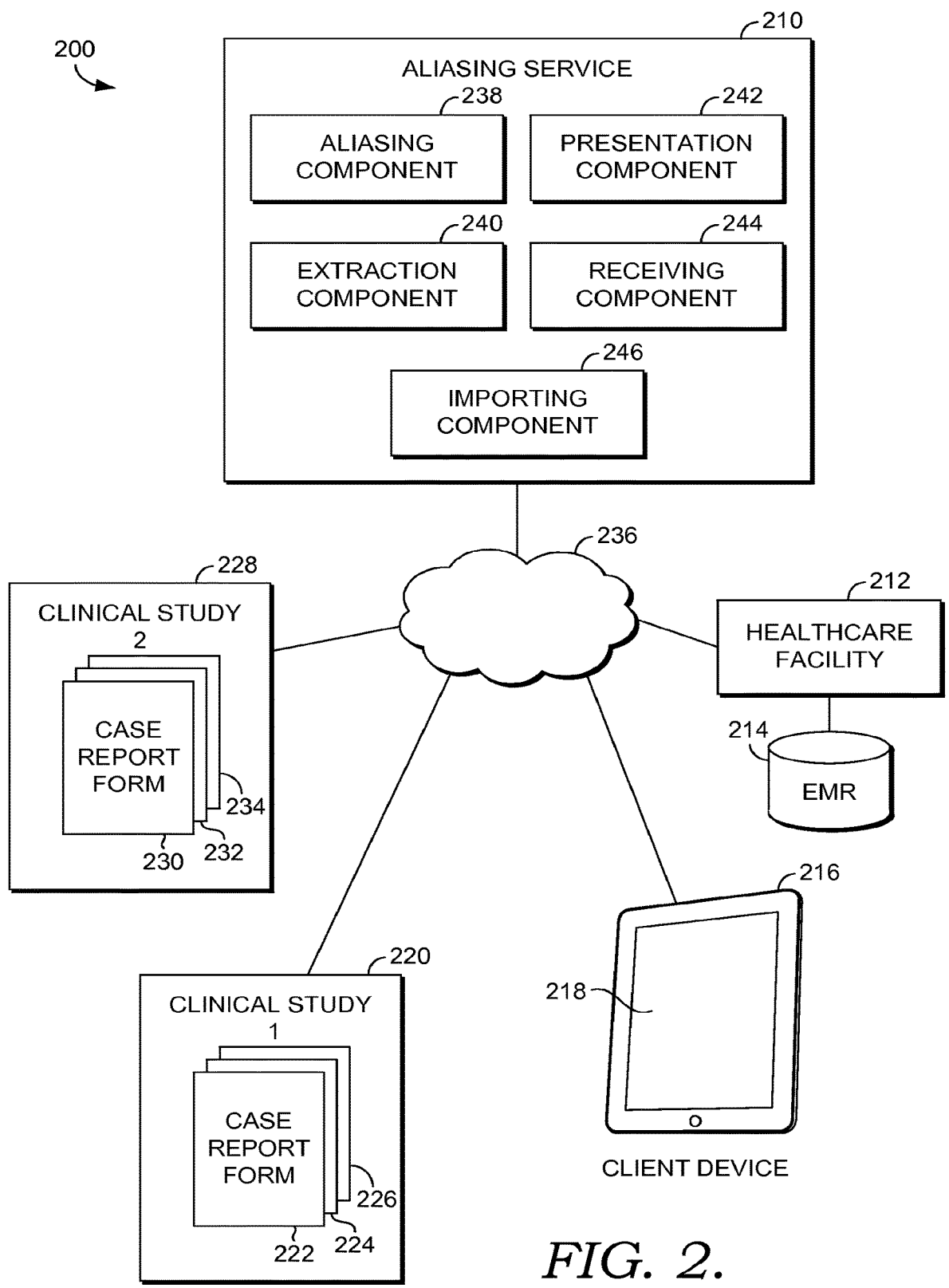
FIG. 2 is a block diagram of an exemplary system for utilizing a generic aliasing scheme to facilitate electronic transcription of clinical event data extracted from an electronic medical record to case report forms associated with clinical studies suitable to implement embodiments of the present invention.

Turning now to FIG. 2, an exemplary computing system environment 200 is depicted suitable for use in implementing embodiments of the present invention. The computing system environment 200 is merely an example of one suitable computing system environment and is not intended to suggest any limitation as to the scope of use or functionality of embodiments of the present invention. Neither should the computing system environment 200 be interpreted as having any dependency or requirement related to any single module/component or combination of modules/components illustrated therein.

The computing system environment 200 includes an aliasing service 210, a healthcare facility 212 and its associated EMR system 214, a client device 216, and two clinical studies 220 and 228, each with its associated case report forms, all in communication with one another via a network 236. The network 236 may include, without limitation, one or more local area networks (LANs) or wide area networks (WANs). Such networking environments are commonplace in offices, enterprise-wide computer networks, intranets, and the Internet. Accordingly, the network is not further described herein.

In some embodiments, one or more of the illustrated components/modules may be implemented as stand-alone applications. In other embodiments, one or more of the illustrated components/modules may be integrated directly into the operating system of the aliasing service 210. The components/modules illustrated in FIG. 2 are exemplary in nature and in number and should not be construed as limiting. Any number of components/modules may be employed to achieve the desired functionality within the scope of embodiments hereof. Further, components/modules may be located on any number of servers. By way of example only, the aliasing service 210 might reside on a server, a cluster of servers, or a computing device remote from one or more of the remaining components.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

The healthcare facility 212 may include, for example, hospitals, physician offices, nursing homes, urgent care clinics, and the like. Although only one healthcare facility is shown, it is contemplated that the present invention may encompass multiple healthcare facilities. The healthcare facility 212 treats patients, one or more of which may be enrolled in a clinical study such as clinical study 220 and/or clinical study 228. In the course of a patient's treatment, clinical event data is collected by the healthcare facility 212 using one or more documentation applications. The clinical event data may be collected in the ordinary course of treating the patient or in response to specific requirements of a clinical study in which the patient is enrolled. The types of clinical event data are numerous but representative examples may include vital signs, physical history, social history, medication history, immunization history, adverse drug event data, laboratory results, radiograph results, and the like. After collection, the clinical event data is stored in association with the EMR system 214.

The healthcare facility 212 may be able to access the aliasing service 210 in a variety of ways within the scope of the present invention. For example, in some embodiments, the healthcare facility 212 may have a native clinical computing system, which may be able to communicate with the aliasing service 210. In other embodiments, a client application associated with the aliasing service 210 may reside or partially reside on one or more of the healthcare facility's computing devices facilitating communication with the aliasing service 210. In further embodiments, communication may simply be a web-based communication, using, for example, a web browser to communicate to the aliasing service 210 via the Internet. Any and all such variations are contemplated to be within the scope of embodiments of the present invention.

The healthcare facility's EMR system 214 may comprise electronic clinical documents such as images, clinical notes, orders, summaries, reports, analyses, or other types of electronic medical documentation relevant to a particular patient's condition and/or treatment. Electronic clinical documents contain various types of clinical event data relevant to the condition and/or treatment of a particular patient and can include information relating to, for example, patient identification information, images, alert history, culture results, physical examinations, vital signs, past medical histories, surgical histories, family histories, histories of present illnesses, current and past medications, allergies, symptoms, past orders, completed orders, pending orders, tasks, lab results, other test results, clinical studies in which the patient is currently enrolled or has been previously enrolled in, patient encounters and/or visits, immunizations, physician comments, nurse comments, other caretaker comments, and a host of other relevant clinical information.

The content and volume of such information in the data store 214 are not intended to limit the scope of embodiments of the present invention in any way. Further, though illustrated as a single, independent component, the data store 214 may, in fact, be a plurality of storage devices, for instance, a database cluster.

As shown, the end-user computing device 216 includes a display screen 218. The display screen 218 is configured to display information to the user of the end-user computing device 216, for instance, information relevant to communications initiated by and/or received by the end-user computing device 216, clinical event data organized by group, and/or the like. Embodiments are not intended to be limited to visual display but rather may also include audio presentation, combined audio/visual presentation, and the like. The end-user computing device 216 may be any type of display device suitable for presenting a graphical user interface.

Such computing devices may include, without limitation, a computer, such as, for example, any of the remote computers 108 described above with reference to FIG. 1. Other types of display devices may include tablet PCs, PDAs, mobile phones, smart phones, as well as conventional display devices such as televisions. Interaction with the graphical user interface may be via a touch pad, a pointing device, and/or gestures.

Clinical study "1" 220 and clinical study "2" 228 represent one or more disparate or related clinical studies in which patients, such as patients cared for by the healthcare facility 212, are enrolled. Although only two clinical studies are shown, it is contemplated that the present invention may encompass numerous clinical studies. The clinical studies 220 and 228 may be administered by organizations that are separate from the healthcare facility 212 or by organizations that are affiliated with the healthcare facility 212. Each clinical study 220 and 228 may collect different types of clinical event data. For example, clinical study 220 may be studying the effects of a new medication on humans and clinical study 228 may be studying the effectiveness of a stroke prevention protocol. Each of these studies would likely collect different types of clinical event data. Each clinical study 220 and 228 has associated case report forms (e.g., case report forms 222, 224, and 226 in the case of clinical study 220, and case report forms 230, 232, and 234 in the case of clinical study 228). After the appropriate clinical event data is extracted from the EMR 214 by the aliasing service 210, the aliasing service 210 populates the data into different fields on the case report forms Like the healthcare facility 212, clinical study 220 and clinical study 228 may be able to access the aliasing service 210 in a variety of ways within the scope of the present invention. For example, in some embodiments, the clinical studies 220 and 228 may have a native clinical computing system, which may be able to communicate with the aliasing service 210. In other embodiments, a client application associated with the aliasing service 210 may reside or partially reside on one or more of the clinical studies' computing devices facilitating communication with the aliasing service 210. In further embodiments, communication may simply be a web-based communication, using, for example, a web browser to communicate to the aliasing service 210 via the Internet. Any and all such variations are contemplated to be within the scope of embodiments of the present invention.

Components of the aliasing service 210 may include a processing unit, internal system memory, and a suitable system bus for coupling various system components, including one or more data stores for storing information (e.g., files and metadata associated therewith). The aliasing service 210 typically includes, or has access to, a variety of computer-readable media.

The computing system environment 200 is merely exemplary. While the aliasing service 210 is illustrated as a single unit, it will be appreciated that the aliasing service 210 is scalable. For example, the aliasing service 210 may in actuality include a plurality of computing devices in communication with one another. Moreover, the data store 214, or portions thereof, may be included within, for instance, the aliasing service 210 as a computer-storage medium. The single unit depictions are meant for clarity, not to limit the scope of embodiments in any form.

As shown in FIG. 2, the aliasing service 210 comprises an aliasing component 238, an extraction component 240, a presentation component 242, a receiving component 244, and an importing component 246. In some embodiments, one or more of the components 238, 240, 242, 244, and 246 may be implemented as stand-alone applications. In other embodiments, one or more of the components 238, 240, 242, 244, and 246 may be integrated directly into the operating system of a computing device such as the remote computer 108 of FIG. 1. It will be understood that the components 238, 240, 242, 244, and 246 illustrated in FIG. 2 are exemplary in nature and in number and should not be construed as limiting. Any number of components may be employed to achieve the desired functionality within the scope of embodiments hereof.

The aliasing component 238 of the aliasing service 210 is configured to generate one or more generic aliasing schemes that can be used to group clinical event data in ways that are useful to a wide variety of disparate clinical studies, such as clinical studies 220 and 228. Using a generic aliasing scheme eliminates the need for clinical studies to generate custom programs—saving both time and money.

The generic aliasing scheme generally includes a first field for specifying an item group alias that describes a clinical event type or group, a second field for specifying an item alias that describes a particular item of clinical event data, and an optional third field used to specify a suffix that describes how the clinical event data within the clinical event group will be grouped. A data collection script can be used to specify the aliases for the item groups and the items; the data collection script maps to data locations in the EMR 214. Several examples will be provided to illustrate generic aliasing schemes and their applications. These examples are not meant to be limiting and additional aliasing schemes beyond these examples are contemplated as being within the scope of the invention.

A generic aliasing scheme that is used to group clinical event data based on the time and the date when the data was collected and stored in the EMR 214 includes:

<ITEM GROUP ALIAS>.<ITEM ALIAS>.DTTM

The same item group alias will be assigned to different items of clinical event data that will be grouped together. The suffix "DTTM" is appended to the item alias and indicates that timestamp information should be extracted from the EMR 214 when the pieces of clinical event data corresponding to the item aliases are extracted, and that the timestamp information should be used to group clinical event data collected on the same day and at the same time.

As a practical example, a clinical study, such as the clinical study 220, may wish to collect information about apical heart rate readings and systolic blood pressure readings recorded for a patient enrolled in the clinical study 220 and group the readings based on the day and time when they were recorded. Using the generic aliasing scheme provided above, a user associated with the clinical study 220 specifies the following aliasing schemes: VS.SYSBP.DTTM and VS.APHR.DTTM, where "VS" is the item group alias for vital signs, "SYSBP" and "APHR" are item aliases for systolic blood pressure and apical heart rate, and "DTTM" is the suffix. As explained further below, these aliasing schemes are used to extract from the patient's EMR systolic blood pressure readings and their associated time stamps, and apical heart rate readings and their associated time stamps. Based on the suffix, those readings that occurred on the same day and at the same time will be grouped together under the item group "vital signs."

Another generic aliasing scheme that is used to indicate whether a task associated with a particular piece of clinical event data was completed, and, if not completed, the reason it was not completed, includes:

<ITEM GROUP ALIAS>.<ITEM ALIAS>.TASK

The same item group alias will be assigned to different clinical event data that will be grouped together. The suffix "TASK" is appended to the item alias and indicates that task completion information, including the time and date when the task was completed, will be extracted from the EMR 214 when the pieces of clinical event data corresponding to the item aliases are extracted, and that the task completion information will be used to group the pieces of clinical event data under the clinical event group. For instance, all pieces of clinical event data on which task completion was documented and having the same item group alias will be grouped together. If a task was not completed for a particular piece of clinical event data, the "TASK" suffix is additionally used to extract information from the EMR regarding the documented reason the task was not completed.

Using another practical example, the clinical study may wish to collect information about whether informed consent was obtained from the patient for participation in the clinical study. Using the generic aliasing scheme for task completion, a user associated with the clinical study specifies the following aliasing scheme, "STUDYINFO.CONSENT-.TASK," where "STUDYINFO" is the item group alias for the clinical study and its associated case report form, "CONSENT" is the item alias for informed consent, and "TASK" is the suffix that indicates that task completion information is needed. The aliasing scheme is used to extract from the patient's EMR information regarding whether informed consent was documented for the clinical study and, if informed consent was documented, a date and time associated with the documentation. If informed consent was not documented, the "TASK" suffix is used to extract any documented reasons why informed consent was not obtained from the patient (e.g., the patient was unconscious and unable to give informed consent).

A third generic aliasing scheme generated by the aliasing component 238 is used to group clinical event data collected together on the same documentation form. The clinical event data may be collected in a grid on the documentation form, or in individual cells on the documentation form. The third generic aliasing scheme corresponds to the following format:

<ITEM GROUP ALIAS>.<ITEM ALIAS>

In this case, the "item alias" in combination with the "item group alias" indicates that clinical event data corresponding to the item alias will be grouped under the clinical event group indicated by the item group alias. For example, a documentation form used by a clinician may have a grid for documenting alcohol use. The grid may include fields for alcohol frequency, alcohol type, and alcohol amount. To collect and group together information about alcohol frequency and alcohol amount, the administrator of the clinical study may specify the following aliasing schemes: ALCOHOL.ALCOHOLFREQ and ALCOHOL.ALCOHOLAMT. These aliasing schemes will be used to extract clinical event data regarding alcohol frequency and alcohol amount from the grid on the documentation form and group the information together under alcohol use. In this case, the grid represents a subset of data items collected on the same documentation form.

In the case where a particular documentation form is used to gather information, but the information is not part of a grid, the same generic aliasing scheme can be used. For example, a documentation form may be used by a clinician to gather a social history for the patient. The form may have fields for marital status, smoking history, education level, and the like. The clinical study may be interested in information regarding marital status and smoking history. The administrator may specify the following aliasing schemes: SOCIALHX.MARITAL and SOCIALHX.SMOKINGHX. The aliasing schemes are used to extract the indicated information from the social history documentation form and group the data together under social history.

Once the generic aliasing schemes have been generated by the aliasing component 238, the receiving component 244 is configured to receive inputs specifying, for example, specific item group aliases and item aliases corresponding to input fields of a particular generic aliasing scheme. The inputs may be specified using, for example, data collection script and may be inputted by a user associated with a clinical study who is seeking to collect information needed by the clinical study.

The extraction component 240 is configured to use the user-specified aliasing scheme(s) to extract clinical event data from the EMR 214 and group the data according to the specified aliasing scheme. In one aspect, the clinical event data is stored in disparate locations within the EMR 214. In another aspect, the clinical event data is stored in association with a particular location within the EMR 214, such as a particular documentation form.

The presentation component 242 is configured to present the extracted groups of data on a user interface of a display device such as the client device 216. Depending of the specified aliasing scheme(s), more than one group of clinical event data may be presented. For instance, using the example given above regarding the aliasing scheme that extracts systolic blood pressure and apical heart rate information from the EMR and groups the readings based on time and date of collection, one of the presented groups may correspond to vital sign readings taken at 8:00 am on Jun. 1, 2013, and another of the presented groups may correspond to vital sign readings taken at 12:00 pm on Jun. 1, 2013.

The receiving component 244 is configured to receive a user selection of one or more of the presented groups. For example, the clinical study may only be interested in readings taken in the morning. The user is able to specify that only the readings taken at 8:00 am on Jun. 1, 2013 should be electronically transcribed into the case report form.

The importing component 246 is configured to electronically transcribe and/or import the selected group of clinical event data to one or more case report forms associated with the clinical study. The importing component 246 uses the specified aliasing scheme to determine which fields on the case report form to import the selected group of data. For instance, the specified item group alias in the aliasing scheme may be "vitals," and the particular case report form has a field corresponding to "vitals." The importing component 246 uses the item group alias to import the vitals group into the vitals field on the case report form. In a further example, the specified item group alias may be "vital signs" and the item alias may be "systolic blood pressure." The importing component 246 uses both the item group alias and the item alias to import the systolic blood pressure reading into the systolic blood pressure field under the vitals field on the case report form.

Figure 3:
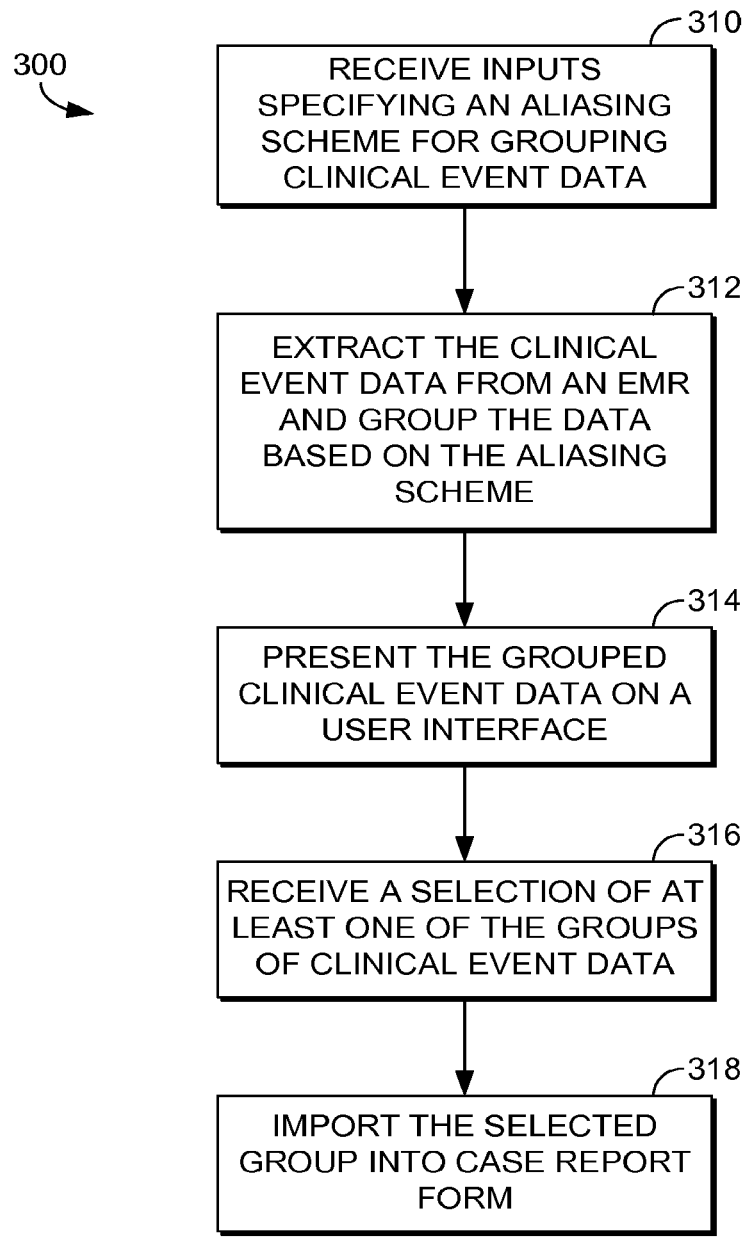
FIG. 3 is a flow diagram of an exemplary method of using a specified aliasing scheme to group a set of clinical event data extracted from an EMR and using the specified aliasing scheme to facilitate electronic transcription of the set of clinical event data into one or more fields of a case report form in accordance with an embodiment of the present invention.

Turning now to FIG. 3, FIG. 3 depicts a flow diagram of an exemplary method 300 of using aliasing schemes to facilitate the electronic transcription of clinical event data extracted from an EMR to case report forms associated with one or more clinical studies. The clinical studies may be disparate from one another and require different types of clinical event data. Further, the clinical studies may require the clinical event data be grouped in a certain way or that task completion be documented. The generic aliasing scheme described in the present invention can be used to meet these different needs without requiring the clinical studies to generate their own custom programs.

At a step 310, inputs are received from, for example, a user associated with the clinical study, specifying an aliasing scheme that is used to group a defined set of clinical event data that is stored in association with an EMR, such as the EMR 214 of FIG. 2. For example, the inputs may comprise an item group alias and one or more item aliases. Thus, the set of clinical event data specified by the item aliases is associated with a particular clinical event type or group specified by the item group alias. The specified aliasing scheme may be derived from a generic aliasing scheme generated by an aliasing component such as the aliasing component 238 of FIG. 2. The aliasing scheme may additionally include a suffix that describes how clinical event data will be grouped. The item group alias and the item alias may be specified using one or more data collection scripts such as, for example, CDASH nomenclature, that map to existing data locations in the EMR.

As described above, suffixes may be used to indicate how the set of clinical event data will be grouped. For example, the "DTTM" suffix is used to group the set of clinical event data based on a date and a time when the data was collected or recorded in the EMR. Another suffix, the "TASK" suffix, is used to group the set of clinical event data based on whether one or more tasks associated with the set of clinical event data were completed. Regarding task completion, if a task was not completed with respect to a certain clinical event, the "TASK" suffix is also used to extract information from the EMR about why the task was not completed. Although a suffix is not used, the set of clinical event data may also be grouped based on a relationship between the data elements within the set and a parent event indicated by the item group alias.

At a step 312, the set of clinical event data is extracted from the EMR by an extraction component, such as the extraction component 240 of FIG. 2, and is grouped according to the specified aliasing scheme. At a step 314, the groups are presented on a user interface by a presentation component, such as the presentation component 242 of FIG. 2. At a step 316, a receiving component (such as the receiving component 244 of FIG. 2) receives a selection of at least one of the presented groups. The selection may be inputted by a user associated with the clinical study. At a step 318, the selected group is electronically transcribed or imported into one or more case report forms associated with the clinical studies by an importing component such as the importing component 246 of FIG. 2. The specified aliasing scheme is further used to facilitate this process. For example, the aliases used in the specified aliasing scheme may correspond to descriptors associated with one or more fields on the case report form. The importing component uses the specified aliasing scheme to direct where data in the selected group should be placed on the case report form.

Figure 4:
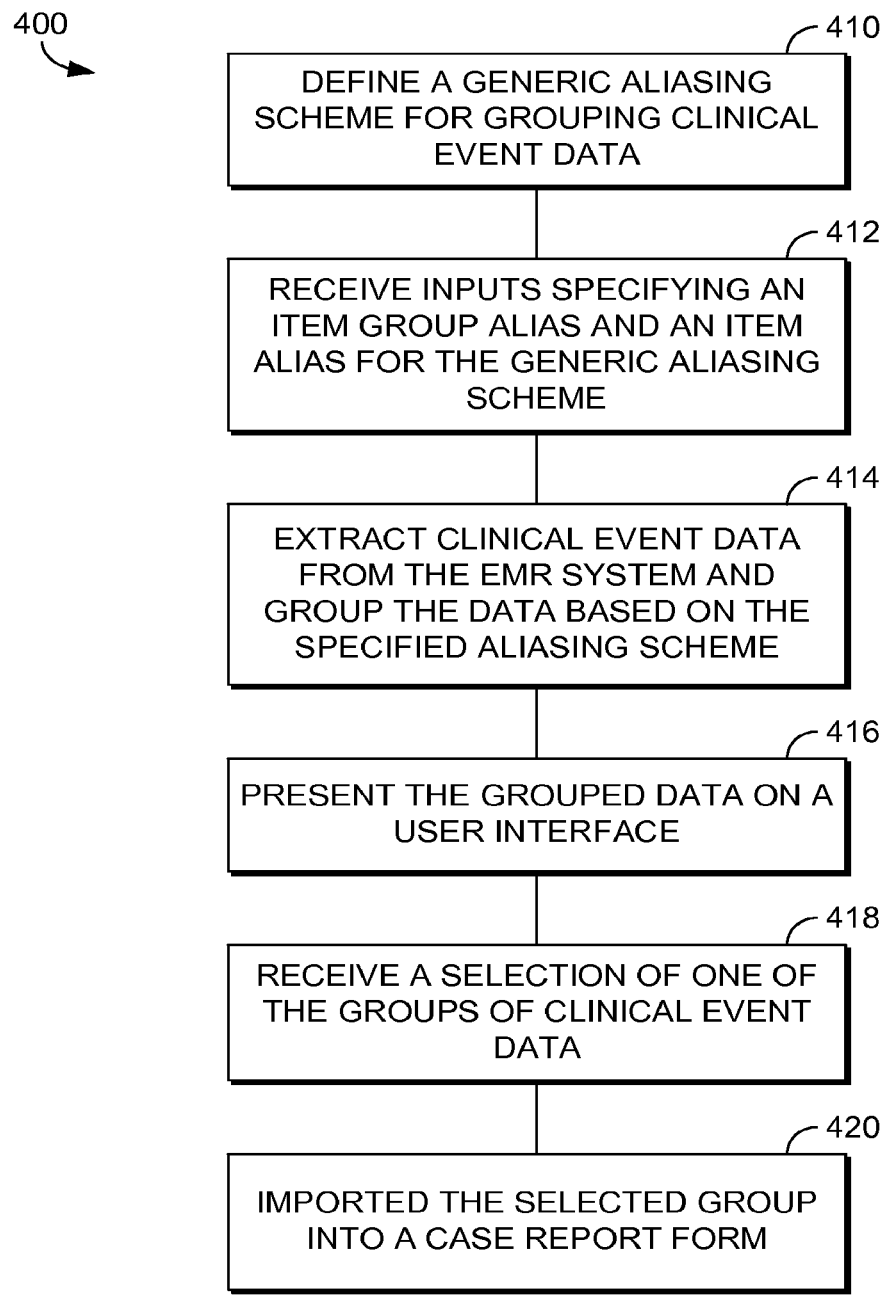
FIG. 4 is a flow diagram of an exemplary method of generating a generic aliasing scheme, receiving inputs specifying parameters for the generic aliasing scheme, and using the specified aliasing scheme to facilitate electronic transcription of groups of clinical event data extracted from an electronic medical record to one or more case report forms associated with disparate clinical studies in accordance with an embodiment of the present invention.

Turning now to FIG. 4, a flow diagram is depicted of an exemplary method of generating a generic aliasing scheme, receiving inputs specifying aliases for the generic aliasing scheme, and using the specified aliasing scheme to facilitate electronic transcription of groups of clinical event data extracted from an electronic medical record to one or more case report forms associated with disparate clinical studies. At a step 410, the generic aliasing scheme is defined by an aliasing component of an aliasing service such as the aliasing component 238 of FIG. 2. The generic aliasing scheme is useable by a plurality of disparate clinical studies and specifies ways to group clinical event data stored in association with an EMR. The generic aliasing scheme comprises at least a first field used for specifying an item group alias corresponding to a clinical event type or group, and a second field used for specifying an item alias that corresponds to a specific item of clinical event data. The generic aliasing scheme may further include an optional third field located after the second field that specifies a suffix that indicates how clinical event data associated with the clinical event group should be grouped.

At a step 412, a receiving component, such as the receiving component 244 of FIG. 2, receives one or more inputs specifying the item group alias and the item alias. The inputs may be received from a user associated with one of the clinical studies. At a step 414, clinical event data is extracted from the EMR based on the specified aliasing scheme, and the extracted data is grouped into one or more groups according to the specified aliasing scheme. At a step 416, the groups are presented on a user interface, and, at a step 418, a selection of at least one of the groups is received. At a step 420, the selected group(s) is imported into one or more of the case report forms. The specified aliasing scheme is used to determine an appropriate field(s) on the case report form to import the selected group.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. A system for providing an aliasing scheme, the system comprising:
   one or more processors; and
   one or more computer storage memory having computer-executable instructions stored thereon that, when executed by the one or more processors, cause the one or more processors to perform operations comprising:
      providing, by a central aliasing service to a remote user device via network communications, a user interface that provides at least a first field and a second field, wherein the central aliasing service is configured to control types of data to be extracted from an electronic medical record (EMR) system based at least on the first field and the second field;
   wherein the central aliasing service is configured with and executes an aliasing component configured to generate a generic aliasing scheme that describes ways to group clinical event data stored in association with the electronic medical record (EMR) system including data records from a plurality of disparate clinical studies that is accessible to the central aliasing service via a computer network, the generic aliasing scheme comprising at least:
   the first field, for specifying an item group alias corresponding to a clinical event group; and
   the second field, for specifying an item alias corresponding to an item of the clinical event data within the clinical event group;
   generating, via the central aliasing service, a first case report form according to the generic aliasing scheme by:
      receiving, a first input specifying the item group alias for the first field and a second input specifying the item alias for the second field to generate a first specified aliasing scheme;

extracting a first set of the clinical event data from the EMR system based on the first specified aliasing scheme;

grouping the extracted first set of clinical event data into one or more first groups based on the first specified aliasing scheme;

presenting the one or more first groups on the user interface;

receiving, a first selection of at least one of the one or more first groups;

determining a first placement, on the first case report form, for the at least one of the one or more first groups associated with the first selection based on the first specified aliasing scheme; and automatically importing, via an importing component of the central aliasing service, the first selection into the determined first placement on the first case report form, wherein automatically importing the first selection comprises using the first specified aliasing scheme, by the one or more processors, to direct the first placement of the first selection into the determined first placement on the first case report form.

2. The system of claim 1, the operations further comprising:

generating, via the central aliasing service, a second case report form utilizing the generic aliasing scheme by:

receiving a third input specifying the item group alias for the first field and a fourth input specifying the item alias for the second field to generate a second specified aliasing scheme;

extracting a second set of the clinical event data from the data records from the EMR system based on the second specified aliasing scheme;

grouping the extracted second set of clinical event data into one or more second groups based on the second specified aliasing scheme;

presenting the one or more second groups on the user interface; receiving a second selection of at least one of the one or more second groups;

determining a second placement, on the second case report form, for the at least one of the one or more second groups associated with the second selection based on the second specified aliasing scheme; and automatically importing, via the importing component of the central aliasing service, the second selection into the determined second placement on the second case report form, wherein automatically importing the second selection comprises using the second specified aliasing scheme to direct the second placement of the second selection into the determined second placement on the second case report form.

3. The system of claim 1, the generic aliasing scheme further comprising a third field that specifies a suffix that indicates how the extracted first set of clinical event data is grouped into the one or more first groups.

4. The system of claim 3, wherein the suffix is "task" and indicates task completion information including a time and date corresponding to when a task associated with the first set of clinical event data was completed.

5. The system of claim 3, wherein the suffix is "task" and indicates task completion information including a documented reason that a task, associated with the first set of clinical event data, was not completed.

6. The system of claim 1, wherein the first specified aliasing scheme is further used to determine an appropriate field on the first case report form during the automatically importing of the first selection.

7. The system of claim 5, further comprising extracting the documented reason that the task was not completed from the EMR system for the first set of clinical event data.

8. The system of claim 1, wherein a first subset and a second subset of the first set of clinical event data are stored in disparate locations within the EMR system.

9. The system of claim 8, wherein the first subset of the first set of clinical event data is different from the second subset of the first set of clinical event data.

10. A method for generating one or more case report forms based on a generic aliasing scheme for grouping clinical event data stored in association with an electronic medical record (EMR) system, the method comprising:

providing, by a central aliasing service to a remote user device via network communications, a user interface that provides at least a first field and a second field, wherein the central aliasing service controls types of data to be extracted from the EMR system based at least on the first field and the second field;

generating, via the central aliasing service in communication with the EMR system, a specified aliasing scheme based on receiving a first input for the first field and a second input for the second field via the user interface;

extracting, via the central aliasing service, the clinical event data from the EMR system based on the specified aliasing scheme;

grouping, via the central aliasing service, the extracted clinical event data into one or more groups;

determining a placement, on the one or more case report forms, for the one or more groups based on the specified aliasing scheme; and automatically importing, via an importing component of the central aliasing service, the one or more groups into the determined placement on the one or more case report forms for presentation, wherein automatically importing the one or more groups comprises using the specified aliasing scheme, by one or more processors, to direct the placement of the one or more groups into the determined placement on the one or more case report forms.

11. The method of claim 10, further comprising receiving a third input for a third field, the third input corresponding to a suffix that indicates how the extracted clinical event data from the EMR system is grouped into the one or more groups.

12. The method of claim 11, wherein the specified aliasing scheme is generated based on the first input, the second input, and the third input.

13. The method of claim 12, wherein the suffix is "dttm" and indicates that the extracted clinical event data is grouped based on a time stamp.

14. The method of claim 13, wherein the extracted clinical event data is grouped into the one or more groups based on the time stamp.

15. The method of claim 10, wherein an alias in the specified aliasing scheme corresponds to a descriptor associated with the determined placement on the one or more case report forms.

16. The method of claim 10, wherein an item group alias of the specified aliasing scheme is "vital signs".

17. The method of claim 10, wherein the extracted clinical event data includes vital signs, social history, and laboratory results.

18. A central aliasing system for creating case report forms, the system comprising:
- a non-transitory memory device for storing computer readable program code; and
- a processor in communication with the memory device, the processor being operative with the computer readable program code to:
  - provide, by the central aliasing system to a remote user device via network communications, a user interface that provides at least a first field and a second field, wherein the central aliasing system controls types of data to be extracted from an electronic medical record (EMR) system based at least on the first field and the second field;
  - define a generic aliasing scheme based on communication with the electronic medical record (EMR) system, the generic aliasing scheme comprising:
    - the first field, for receiving a first input via the user interface, for specifying an item group alias corresponding to a clinical event group; and
    - the second field, for receiving a second input via the user interface, for specifying an item alias corresponding to an item of clinical event data within the clinical event group;
  - generate, by the processor, a case report form utilizing the generic aliasing scheme by:
    - receiving the first input specifying the item group alias;
    - receiving the second input specifying the item alias;
    - generating a specified aliasing scheme using the first input and the second input to control data extraction and data placement;
    - extracting a first set of the clinical event data based on the specified aliasing scheme from the electronic medical record (EMR) system;
    - grouping the extracted first set of clinical event data into one or more groups;
    - determining a placement, on the case report form, for the one or more groups based on the specified aliasing scheme; and
    - automatically importing, via an importing component of the central aliasing system, the one or more groups into the determined placement on the case report form, wherein automatically importing the one or more groups comprises using the specified aliasing scheme, by the processor, to direct the placement of the one or more groups into the determined placement on the case report form.

19. The system of claim 18, wherein the generic aliasing scheme further comprises a third field that specifies a suffix.

20. The system of claim 19, wherein the specified aliasing scheme is generated based on receiving a third input at the third field in addition to the first input and the second input.

* * * * *